United States Patent
Krüger (10) Patent No.: US 10,555,759 B2
(45) Date of Patent: *Feb. 11, 2020

(54) POLYAXIAL PEDICLE SCREW HAVING PROVISIONAL FASTENING MEANS

(71) Applicant: Aesculap AG, Tuttlingen (DE)

(72) Inventor: Sven Krüger, Trossingen (DE)

(73) Assignee: Aesculap AG (DE)

( * ) Notice: Subject to any disclaimer, the term of this patent is extended or adjusted under 35 U.S.C. 154(b) by 24 days.

This patent is subject to a terminal disclaimer.

(21) Appl. No.: 15/432,111

(22) Filed: Feb. 14, 2017

(65) Prior Publication Data

US 2017/0172627 A1 Jun. 22, 2017

Related U.S. Application Data

(63) Continuation of application No. 14/241,492, filed as application No. PCT/EP2012/064207 on Jul. 19, 2012, now Pat. No. 9,603,627.

(30) Foreign Application Priority Data

Sep. 6, 2011 (DE) .................. 10 2011 053 295

(51) Int. Cl.
*A61B 17/70* (2006.01)
*A61B 17/00* (2006.01)

(52) U.S. Cl.
CPC ...... *A61B 17/7032* (2013.01); *A61B 17/7002* (2013.01); *A61B 17/708* (2013.01);
(Continued)

(58) Field of Classification Search
CPC ............ A61B 17/7032; A61B 17/7034; A61B 17/708; A61B 17/7002; A61B 17/7035; A61B 17/7037

See application file for complete search history.

(56) References Cited

U.S. PATENT DOCUMENTS 3,964,364 A 6/1976 Poe
4,007,516 A 2/1977 Coules
(Continued)

FOREIGN PATENT DOCUMENTS

AU 2003287273 B2 6/2004
AU 2005305193 5/2006
(Continued)

OTHER PUBLICATIONS

Notice of Allowance for U.S. Appl. No. 13/558,777, dated Oct. 17, 2017, 5 pages.
(Continued)

*Primary Examiner* — Ellen C Hammond
(74) *Attorney, Agent, or Firm* — RatnerPrestia (57) ABSTRACT

A polyaxial pedicle screw includes a screwed shaft section for anchoring the pedicle screw in a vertebra, on one axial end of which a shaft head is configured which is coupled in a rotating and/or pivoting manner as well as in a tensile-force transmitting manner to a receiving sleeve for a longitudinal support. The receiving sleeve has a fastening means for selective positional fastening of the receiving sleeve with respect to the shaft section, the fastening means at least consisting of an inlay/pin mounted in the receiving sleeve and acting on the shaft head, and a locking element acting on the inlay/pin. The inlay/pin is configured with attachment points or engagement elements, which are not covered or overlapped by the locking element, for the provisional introduction of a compressive force on the inlay/pin parallel to the locking element.

20 Claims, 5 Drawing Sheets

(52) U.S. Cl.
CPC ...... *A61B 17/7035* (2013.01); *A61B 17/7037* (2013.01); *A61B 2017/0023* (2013.01)

(56) References Cited

U.S. PATENT DOCUMENTS

| | | | |
|---|---|---|---|
| 4,085,651 A | 4/1978 | Koscik | |
| 4,602,496 A | 7/1986 | Wagener | |
| 5,323,664 A | 6/1994 | Fairfeild | |
| 5,499,985 A | 3/1996 | Hein | |
| 6,045,309 A | 4/2000 | LeVey | |
| 6,063,090 A | 5/2000 | Schlapfer | |
| 6,183,472 B1 | 2/2001 | Lutz | |
| 6,540,461 B1 | 4/2003 | Hawang | |
| 7,491,218 B2 | 2/2009 | Landry | |
| 8,496,706 B2 | 7/2013 | Ragab | |
| 8,636,740 B2 | 1/2014 | Weaver | |
| 2004/0122425 A1 | 6/2004 | Suzuki | |
| 2004/0172022 A1 | 9/2004 | Landry | |
| 2005/0123379 A1 | 6/2005 | Barina | |
| 2005/0131408 A1 | 6/2005 | Sicvol | |
| 2005/0192579 A1 | 9/2005 | Jackson | |
| 2006/0036244 A1 | 2/2006 | Spitler | |
| 2006/0074418 A1 | 4/2006 | Jackson | |
| 2006/0074421 A1 | 4/2006 | Bickley | |
| 2006/0084993 A1 | 4/2006 | Landry | |
| 2006/0095035 A1 | 5/2006 | Jones | |
| 2006/0111715 A1 | 5/2006 | Jackson | |
| 2006/0142761 A1 | 6/2006 | Landry | |
| 2006/0247658 A1 | 11/2006 | Pond | |
| 2007/0219554 A1 | 9/2007 | Landry | |
| 2007/0239159 A1 | 10/2007 | Altarac | |
| 2007/0239279 A1 | 10/2007 | Francis | |
| 2007/0260246 A1 | 11/2007 | Biedermann | |
| 2008/0039838 A1 | 2/2008 | Landry | |
| 2008/0039840 A1 | 2/2008 | Songer | |
| 2008/0045956 A1 | 2/2008 | Songer | |
| 2008/0045957 A1 | 2/2008 | Landry | |
| 2008/0077139 A1 | 3/2008 | Landry | |
| 2008/0154277 A1 | 6/2008 | Machalk | |
| 2008/0215100 A1 | 9/2008 | Matthis | |
| 2008/0215510 A1 | 9/2008 | Regli | |
| 2009/0012567 A1 | 1/2009 | Biedermann | |
| 2009/0157125 A1 | 6/2009 | Hoffman | |
| 2009/0171391 A1 | 7/2009 | Hutton | |
| 2009/0228053 A1 | 9/2009 | Kolb | |
| 2009/0318972 A1 | 12/2009 | Jackson | |
| 2011/0077690 A1 | 3/2011 | Shin | |
| 2011/0278487 A1 | 11/2011 | King | |
| 2012/0031179 A1 | 2/2012 | Petit | |
| 2012/0143266 A1* | 6/2012 | Jackson | A61B 17/7008 606/328 |
| 2012/0245640 A1* | 9/2012 | Auerbach | A61B 17/7035 606/264 |
| 2013/0018419 A1 | 1/2013 | Rezach | |
| 2013/0096623 A1 | 4/2013 | Biedermann | |
| 2014/0094917 A1 | 4/2014 | Salerni | |
| 2014/0316468 A1 | 10/2014 | Keiser | |

FOREIGN PATENT DOCUMENTS

| | | |
|---|---|---|
| AU | 2003287273 | 6/2007 |
| AU | 2008276119 | 1/2009 |
| AU | 2009201461 | 5/2009 |
| AU | 2003287273 C1 | 1/2010 |
| CA | 2502571 | 5/2004 |
| CA | 2586554 | 5/2006 |
| DE | 29806563 | 6/1998 |
| DE | 10157814 | 6/2003 |
| EP | 1558157 | 5/2004 |
| EP | 1835860 | 5/2006 |
| EP | 2301458 | 3/2011 |
| EP | 2502594 | 9/2012 |
| JP | 2007513744 | 5/2007 |
| JP | 2007514512 | 6/2007 |
| JP | 2011514830 | 5/2011 |
| WO | 9825534 | 6/1998 |
| WO | 2005058141 | 6/2005 |
| WO | 2005058386 | 6/2005 |
| WO | 2009055026 | 4/2009 |
| WO | 2009114422 | 9/2009 |

OTHER PUBLICATIONS

Japanese Office Action for Japanese Application No. 2014527549, dated Jun. 7, 2016 with translation—7 Pages.
European Office Action for European Application No. 12 737 556.6, dated Jun. 30, 2016 with translation—11 Pages.
Office Action dated Sep. 23, 2015 for U.S. Appl. No. 13/558,777.
Final Office Action dated Dec. 23, 2015 for U.S. Appl. No. 13/558,777.
International Preliminary Report on Patentability and Written Opinion issued in International Application No. PCT/US2012/048266, dated Feb. 13, 2014.
International Application Serial No. PCT/US2012/048266, International Search Report and Written Opinion dated Nov. 15, 2012.
International Application Serial No. PCT/US2012/048266, International Search Report dated Sep. 13, 2012, 6 Pages.
German Search Report issued in related German Application No. 10 2011 053 295.1, dated May 8, 2012 (with English language description of category codes).

* cited by examiner

POLYAXIAL PEDICLE SCREW HAVING PROVISIONAL FASTENING MEANS

RELATED APPLICATIONS

This application is related to and a continuation of U.S. application Ser. No. 14/241,492, filed Apr. 23, 2014, which is the national phase of International Application No. PCT/EP2012/064207, filed Jul. 19, 2012, which is related to and claims the benefit of priority of German Application No. DE 10 2011 053 295.1, filed Sep. 6, 2011. The contents of U.S. application Ser. No. 14/241,492, International Application No. PCT/EP2012/064207 and German Application No. DE 10 2011 053 295.1 are incorporated by reference herein in their entireties.

FIELD

The present invention relates generally to a polyaxial pedicle screw, and more specifically to a polyaxial pedicle screw having provisional/temporary fastening means, a helping means/tool for the provisional fastening of the polyaxial pedicle screw and also a stabilization system featuring a pedicle screw according to the invention, the helping means according to the invention and also preferably a longitudinal member.

BACKGROUND

Pedicle screws are used principally for the dorsal stabilization of the spinal column in the case of fractures, tumours, infections, deformities and degenerative instabilities by means of a transpedicular screw fixing. Pedicle screws are thereby placed in the pedicles of each adjacent vertebrae, whereupon an angularly-stable connection is created between the pedicle screws which are arranged axially above each other and an axially extending longitudinal member or bar. The pedicle screws and longitudinal member thereby form a vertebra stabilization system.

For this purpose, a pedicle screw generally has an axial, shaft-shaped externally threaded portion to which a so-called tulip is connected on the screw head side. This forms constructively a U-shaped longitudinally slotted/tunnelled receiving sleeve with internal thread, wherein the two longitudinal slots lying radially opposite each other each define a slot gap of predetermined gap width. The longitudinal member is transversely inserted in the longitudinal slots which run parallel to each other, and fixed by means of a locking element, for example a grub screw or threaded nut, which is screwed into the internal thread.

In principle two basic types of pedicle screw are distinguished, namely monoaxial and polyaxial pedicle screws. In the case of a monoaxial pedicle screw, the externally threaded portion or shaft and the tulip are integrally formed with each other such that they are basically fixedly connected to each other, for example welded or soldered. By contrast a polyaxial pedicle screw has, as a separate shaft member, a manufactured externally threaded portion having a mostly spherical or (semi-)spherical screw head which is encompassed relatively pivotably and at the same time grasped from behind by the sleeve-shaped tulip, in the transition region between head and shaft. In this way, after sinking of the externally threaded portion in the pedicle channel of a vertebra, the tulip can be pivoted and/or turned relative to the shaft so as to obtain a desired position and orientation which is essentially independent of the orientation of the shaft. In this way the undercut prevents the tulip from being able to be pulled off from the shaft head. Subsequently the tulip is positionally fixed to the screw head by means of the grub screw in the case of a temporarily fixed bar (one-screw principle) or though an additional screw/nut (multi-screw principle).

Pedicle screws are put in place in the pedicle channel of a vertebra or anchored through screwing, by a surgeon. In doing so the operator aligns the screws on the basis of the orientation of the pedicle channel. When the screws are set, the above mentioned longitudinal member or bar of the correct length is selected, and optionally its longitudinal curvature is adjusted to the pedicle screws and its respective position is also adjusted. The longitudinal member should in addition be placed in the tulips of the pedicle screws.

The polyaxial pedicle screws distinguish themselves henceforth in that the tulip/receiving sleeve is at first movably placed with respect to the screw shaft such that the receiving sleeve can take on a different orientation from the shaft. This makes it easier for the surgeon to laterally insert/guide the longitudinal member in the receiving sleeve. When the surge is satisfied with the seating of the longitudinal member and the receiving sleeve, he locks the pedicle screw by means of the locking element, preferably by means of the grub screw (in principle also termed set screw of any configuration).

The polyaxial locking (positional fixing of the receiving sleeve with respect to the shaft) as well as the clamping of the longitudinal member are locked upon tightening of the set screw in a single assembly step in the case of the above-mentioned one-screw principle.

In the case of polyaxial screws it is generally not possible during the implanting procedure to introduce forces from the receiving sleeve to the vertebra due to the mobility (link) between the screw shaft and the receiving sleeve, in order to manipulate them for example. However this is required in particular with repositioning manoeuvres in the case of fractures or spondylolisthesis and partly with compressions or distractions. For this purpose therefore the monoaxial pedicle screws are used, whereby the receiving sleeve is rigid with the screw shaft. However these monoaxial pedicle screws have the disadvantage that the longitudinal member can only with difficulty be laterally introduced into the tulip/receiving sleeve of several monoaxial pedicle screws.

A polyaxial pedicle screw according to the above mentioned one-screw principle is known from the prior art, for example according to EP 2 301 458 A1, consisting of a shaft member having external thread and spherical head as well as a U-shaped longitudinally slotted receiving sleeve (tulip) for a longitudinal support/bar. The receiving sleeve has an internal thread in the axial region towards the opening of the longitudinal slots, in which a grub screw can be screwed, and a radially inwardly oriented circumferential projection or land in the axial region up to the respective slot base. Furthermore a type of piston or inlay is inserted in the receiving sleeve by means of a snap ring and in this way secured against falling out.

For the assembly of the polyaxial pedicle screw known from EP 2 301 458 A1, the receiving sleeve is first passed from the distal end (the end lying opposite the shaft head) of the shaft member over this shaft member until the radial internal land of the receiving sleeve buts against the shaft head (on its under side). Subsequently the inlay is pushed into the receiving sleeve (i.e. on the upper side of the shaft head) such that the spring ring which is arranged circumferentially between receiving sleeve and inlay snaps into corresponding circumferential grooves on the inlay and on the receiving sleeve, and axially holds both components together. The shaft head is therefore arranged between the land of the receiving sleeve and the inlay (i.e. underneath the inlay).

As soon as the pedicle screw is screwed into a vertebra and fixedly anchored into it, a longitudinal member is introduced into the U-shaped (double) slot of the receiving sleeve (above the inlay), wherein the receiving sleeve can turn and pivot relative to the anchored shaft member. In this way it is possible for an operator to adjust the receiving sleeve to correspond to the orientation of the longitudinal member. As soon as the suitable relative position of the receiving sleeve is set, the grub screw is screwed into the receiving sleeve until it locates the longitudinal member against the inlay and presses this further in the axial direction of the receiving sleeve against the shaft head. In this way the entire pedicle screw/longitudinal member system (vertebra-stabilization system) can be fixed/locked in the set position by tightening the single grub screw (locking element).

US 2008/02155100 A1 discloses for example a polyaxial pedicle screw according to the above mentioned multi-screw principle. This pedicle screw also has a shaft-shaped externally threaded portion having an integral shaft head at a proximal end of the shaft. The shaft head is freely rotatably and pivotably surrounded by a receiving sleeve, in which an internal thread is also configured and which comprises two U-shaped longitudinal slots which lie opposite each other, for a longitudinal member.

A piston/inlay is axially movably inserted in the receiving sleeve, which likewise comprises a U-shaped longitudinal slot with the approximate slot width dimension of the longitudinal slots in the receiving sleeve. The flanks that occur here at the U-shaped longitudinal slot of the inlay are elongated in the axial direction such that they protrude over a bar/longitudinal member transversely inserted in it. In other words the length of the flanks of the inlay is larger than the diameter of the transversely inserted bar/longitudinal member.

In order to assemble the pedicle screw known from US 2008/02155100 A1, the receiving sleeve/tulip is passed over the shaft in a known manner until this axially bears on the shaft head (on the underside) in a pivotable and rotatable manner. Subsequently the inlay (above the shaft head) is introduced into the receiving sleeve and its U-shaped slot aligned corresponding to the U-shaped slots in the receiving sleeve. After a longitudinal member/bar has been introduced into the U-shaped slot of the inlay (and inevitably here also into the slots of the receiving sleeve), a first screw (screw sleeve), preferably a grub screw which was previously screwed into the internal thread of the receiving sleeve, is further tightened in order to press the inlay directly against the shaft head and thus to fix the position of the receiving sleeve relative to the shaft. The longitudinal member however remains initially uninfluenced by the first screw, i.e. not fixed. In this assembly state it is possible to apply an adjusting force via the receiving sleeve to the vertebra.

The first screw is likewise sleeve-shaped and has an internal thread into which a second screw (grub screw) is screwed. The longitudinal member is now fixed in the inlay by means of this second screw, in which the second screw is rotated relative to the first screw and presses directly against the bar in order to clamp said bar in the inlay. In this way the polyaxiality of the pedicle screw is locked and therefore the longitudinal member is also fastened.

In the case of many pedicle screws according to the above mentioned construction, the fastening means/locking elements (screws) are essentially self-lockingly executed in order not to risk an undesired loosening of the longitudinal member from the pedicle screws after implanting. In addition the fixing forces between pedicle screw and longitudinal member are considerable because the entire system must withstand large loads without the set positional relationship between shaft, sleeve and longitudinal member being allowed to change. It follows that the clamping forces between the shaft head and the receiving sleeve are likewise very high such that the frictional fit which forms in-between does not frequently come loose even when the fastening means is released. These requirements however also cause problems during the implanting procedure.

As long as the receiving sleeve is not fixedly (by frictional fit) connected with the shaft head, an adjusting force cannot be transmitted via this receiving sleeve to the vertebra. In other words, in the case of a polyaxial pedicle screw according to the one-screw principle for example, a longitudinal member would first have to be inserted and then the locking element, preferably the grub screw, would have to be tightened in order to be able to finally exert an adjusting force on the vertebra. This however would not be technically sensible.

If an operator first of all has tightened the locking element (for example the grub screw) with force and there might arise afterwards the need of a post-adjustment, the positional relationship fixed in this way is not modifiable again, or only with great difficulty. Expressed in other words, for this purpose the operator would have to release again, against their self-locking effect, the grub screw(s) which have been tightened with great force, without releasing or even breaking the externally threaded portion which is already anchored in the vertebra. Even if the grub screw can be released without problems, a possible self-locking frictional fit is configured between the shaft head and the receiving sleeve. This could be released only through significant force effort (impacts on the receiving sleeve, etc.), even in the case of a released grub screw. Furthermore the locking element's self-locking effect is possibly impaired due to its subsequent loosening, such that the operability of the pedicle screw is no longer ensured.

To this extent, it would be advantageous in principle if the polyaxiality is only provisionally fixable in particular in the case of the one-screw principle, in order to be able to at least temporarily and independently lock the polyaxiality and the bar/longitudinal member. In other words, it would be useful in the case of a polyaxial pedicle screw, also one according to the one-screw principle, to fix by means of a special helping means to be used temporarily only the polyaxiality without the bar being fixed. This would have the advantage that now also the polyaxial pedicle screw would be suited to transmit, before fastening the longitudinal member, correspondingly high forces to the vertebra for its manipulation during the implanting procedure without the inner structure of the pedicle screw becoming significantly more complicated.

It should be noted at this point that the term "provisional", in particular in view of the invention described below, should not necessarily mean only a light fitting/seizing of the shaft head, rather it is understood in particular to mean such a locking measure which is temporarily used and also whose achievable locking properties such as the clamping force on the shaft head etc. thoroughly correspond to the permanent locking means and can at least approach or even exceed this. Expressed in other words the "provisional" locking means should be dimensioned such that it causes a locking of the receiving sleeve at the shaft head corresponding to the permanent locking element. In this case of an optional subsequent loosening of the frictional fit in accordance with the prior art, it would be possible only though considerable force exertion, however there would be at least the possibility of vertebral readjustment before fastening the longitudinal member. Alternatively, it would also be desirable to dimension the "provisional" locking means such that sufficient adjusting forces are transmittable on the vertebra by means of the polyaxial pedicle screw, wherein the frictional fit achieved here between shaft head and receiving sleeve is releasable again.

However the polyaxial pedicle screws according to the described prior art prove themselves to be unfavourable. Therefore in particular in the case of the one-screw principle the polyaxiality can be locked only when the longitudinal member sits (not yet fixed) in its end position. An inserting of the longitudinal member after the locking of the polyaxiality is actually not possible or is only very difficult and would have as a prerequisite a clearly more complicated construction of the pedicle screw.

SUMMARY

In light of the above described problems, it is an object of the invention to increase the functionality a polyaxial pedicle screw, in particular by combining the benefits of a monoaxial pedicle screw with those of a polyaxial pedicle screw. It is an object to allow the manipulability of a vertebra via the polyaxial pedicle screw (according to any execution principle) without the inserting of the longitudinal member into the tulip becoming unduly difficult. Furthermore the polyaxial pedicle screw should not have a (substantially) more complicated construction than the prior art.

The stated object is solved by a polyaxial pedicle screw having provisional/temporary fastening means (in the sense of the above definition) according to claim 1, a helping means/tool for the provisional fastening (in the sense of the above definition) of the polyaxial pedicle screw as well as a stabilization system consisting of the pedicle screw according to the invention and the helping means according to the invention. Advantageous further developments of the invention are substantially the object of the dependent claims.

The basic idea of the invention is essentially based on causing the provisional/temporary fixing (locking) of the polyaxiality by means of an external helping means, which, parallel to the actual (permanent) locking element of the polyaxial pedicle screw, acts (preferably with comparable force) on the inlay and the receiving sleeve in order to bias these against each other and thereby clamp the shaft head which is arranged between inlay and receiving sleeve (in accordance with the actual locking element). The inlay and the receiving sleeve are consequently provided/equipped with engagement elements for the helping means, with which the helping means respectively engages (with force-locking fit), in order to apply a corresponding biasing force on the elements concerned (inlay and receiving sleeve). The engagement element at the inlay is in addition prepared for the application of a compressive force and the engagement element on the receiving sleeve is prepared for the application of a tensile force.

Expressed in other words the (external) helping means according to the invention can be designed such that, with its temporary use as described above, it at times replaces or simulates the actual locking element with reference to the fastening of the polyaxiality, and creates a frictional fit between shaft head and receiving sleeve, which, depending on the desired setting, is bigger or marginally smaller than the frictional fit achieved through the permanent locking element. This means therefore that the term "temporary" should not be understood to the effect that the frictional fit achieved through the helping means is necessarily releasable again, rather that the helping means for the provisional creation of the (releasable or no longer releasable) frictional fit is deployed parallel to the permanent locking element temporarily.

Constructively the above-mentioned basic idea is essentially implemented by the inlay being formed such that it projects or is exposed at least in portions radially over the employed locking element, whereby at these radial portions which are not covered/overlapped by the locking element, attachment points occur for the introduction of a compressive force on the inlay parallel to the actual locking element. Conversely the receiving sleeve is configured/provided with engagement undercuts 11A which are formed/suited for the external introduction of a tensile force.

More specifically the polyaxial pedicle screw according to the invention has a screwed shaft section for anchoring the pedicle screw in a vertebra, on one axial end of which a (spherical or semi-spherical) shaft head is configured. The shaft head is coupled in a rotating and/or pivoting manner with a receiving sleeve for a longitudinal support, wherein the receiving sleeve comprises a fastening means for the selective positional fastening of the receiving sleeve with respect to the shaft section. The fastening means has an inlay which is mounted in the receiving sleeve and acts on the shaft head, and a locking element acting on the inlay, whereby the inlay is biasable against the shaft head and thereby the shaft head clamps (by frictional fit) between the inlay and the receiving sleeve which engages behind the shaft head (with form-locking fit). According to a first aspect of the invention, the inlay is configured/provided with attachment points or engagement elements, which are not covered or overlapped by the locking element, for the introduction of a (provisional/temporary) compressive force on the inlay parallel to the locking element, preferably using a separate tool-like helping means.

Another aspect of the invention provides that the inlay is formed such that it projects or is exposed, at least in portions, radially over the locking element, whereby the attachment points occur (for the separate helping means) at these radial portions which are not covered or overlapped by the locking element.

It can be advantageous when the inlay has an outline deviating from a circle, preferably an oval outline, at least at one axial (inlay) portion whereby those outline portions with large diameter protrude radially over the locking element and contain the attachment points. Alternatively here it is also possible to form radially projecting lugs at the inlay, or even to give a many-cornered profile to the inlay, whereby outline areas occur which protrude radially over the locking element which is preferably a screw/grub screw. In this way a separate helping means/tool for the provisional/temporary fastening at least of the polyaxiality can be guided along to the (not yet locked) locking element and be brought into axial compressive engagement with the inlay.

Preferably the attachment points are marked by axial centering holes which serve for the receiving and placement of an external helping means for the application of pressure to the inlay. Thus the helping means cannot slide off from the inlay and the projecting outline portions of the inlay can be designed to be relatively small.

In order to be able to exert a sufficiently large provisional/temporary fixing force on the inlay (comparable to the actual locking element) it is advantageous when the inlay and the receiving sleeve are biasable against each other by means of the separate helping means. To this aim the receiving sleeve may be configured or provided with at least one engagement element via which an external provisional tensile force parallel to the locking element can be applied to the receiving sleeve. Preferably the engagement element is an engagement undercut 11A which further preferably is formed on the external sleeve-side of the receiving sleeve. This has the advantage of the radial displacement of that member of the helping means which should apply a compressive force on the inlay, from that member with which a (counter) tensile force is exerted on the receiving sleeve. Thereby both members of the helping means can be placed almost one inside the other, whereby this becomes very compact and also stable.

Another aspect of the invention relates to a helping means for the provisional/temporary fastening of the polyaxiality of a pedicle screw such as the one described above. The helping means, provided as a separate tool, has a first member preferably in the form of a plunger for coming into pressing engagement with the attachment points provided at the inlay and a second member, preferably a pulling member which is movable relative to, preferably in opposition to, the first member and has a latching or clasping means which can be brought into pulling engagement with the receiving sleeve, preferably at its engagement element. Preferably the pulling member is a sleeve surrounding the plunger wherein, at an axial end of the sleeve, radially inwardly protruding latching projections, hooks or ledges are formed in order to make releasable latching engagement with the receiving sleeve, preferably at the receiving sleeve's engagement elements. Furthermore the sleeve is preferably operatively connected with the plunger on an axial end section lying opposite the latching protrusions via a coupling. This coupling causes a compressive force from the plunger to be converted into a tensile force from the surrounding sleeve whereby there arises a provisional/temporary closed flow of forces between inlay, shaft head, receiving sleeve and separate helping means. The anchoring of the pedicle screw in the vertebra remains unaffected from this.

Another aspect of the invention relates to a stabilization system that has the following components:
  a polyaxial pedicle screw at least consisting of a screwed shaft having shaft head surrounded and grasped from behind by a receiving sleeve in which is mounted an inlay biasable against the shaft head by means of a locking element which is preferably screwable into the receiving sleeve and
  a manually operatable helping means, preferably of a tool type, which has a first member for the selective (provisional/temporary) application of pressure to the inlay and a second member for the selective (provisional/temporary) tensile loading of the receiving sleeve (as counter-reaction to the provisional application of pressure), which is parallel to the locking element in each case.

Preferably the stabilization system of the invention further has
  a longitudinal member which is insertable in a transverse slot of the receiving sleeve, wherein at least the first member and preferably also the second member of the helping means is/are designed (preferably having U-shaped longitudinal slots) so that it/they engage/s around the longitudinal member such that the longitudinal member can then still be introduced when the helping means is already set and activated.

Another aspect of the invention relates to a polyaxial pedicle screw having a screwed shaft section for anchoring the pedicle screw in a vertebra. A shaft head is configured at an axial end of the shaft section, and the shaft head is pivotably and/or rotatingly coupled to a receiving sleeve for a longitudinal support. The receiving sleeve includes a fastening means for selective positional fastening of the receiving sleeve with respect to the shaft section. The fastening means includes at least an inlay mounted in the receiving sleeve and acting on the shaft head, and a locking element acting via the longitudinal support on the inlay and screwed directly into the receiving sleeve. The inlay is configured with inlay engagement elements, which are not covered or overlapped by the locking element nor by the longitudinal support, for the introduction of a provisional compressive force parallel to the locking element on the inlay.

Another aspect of the invention relates to a receiving sleeve that includes a sleeve body open on both sides whose sleeve wall is slotted in a U-shape, starting from a proximal end face, whereby there occur two flanks lying radially opposite each other, wherein the inlay engagement elements are located between the two flanks.

Another aspect of the invention relates to an inlay that is formed such that it projects or is exposed, at least in portions, radially over the locking element, whereby the inlay engagement elements occur at these radial portions which are not covered or overlapped by the locking element.

Another aspect of the invention relates to a pedicle screw, wherein the inlay has an outline deviating from a circle, preferably an oval outline, at least at one axial portion whereby outline portions of large diameter protrude radially over the locking element and contain the inlay engagement elements.

Another aspect of the invention relates to a polyaxial pedicle screw, wherein the attachment points are marked by axial centering holes which serve for the receiving and placement of an external helping means for the provisional application of pressure to the inlay.

Another aspect of the invention relates to a polyaxial pedicle screw, wherein the inlay is formed essentially by an inlay sleeve, one end face of which is widened to a flange-like, oval or rectangular collar.

Another aspect of the invention relates to a polyaxial pedicle screw, wherein radially projecting lugs are configured at the inlay at the corners of the rectangular collar, wherein the radially projecting lugs constitute the inlay engagement elements.

Another aspect of the invention relates to a polyaxial pedicle screw, wherein the inlay diametrically connects both of the U-shaped slots in the sleeve body.

Another aspect of the invention relates to a polyaxial pedicle screw, wherein the receiving sleeve is configured or provided with at least one receiving sleeve engagement element via which an external provisional tensile force parallel to the locking element can be applied to the receiving sleeve.

Another aspect of the invention relates to a polyaxial pedicle screw, wherein the receiving sleeve engagement element forms an engagement undercut 11A on an external sleeve-side of the receiving sleeve.

Another aspect of the invention relates to a polyaxial pedicle screw, wherein the inlay engagement elements are configured as inlay engagement elements having form-locking fit.

Another aspect of the invention relates to a helping means for the provisional fastening of the polyaxiality of a pedicle screw which has a screwed shaft having a shaft head which is surrounded by a receiving sleeve in which is mounted an inlay biasable against the shaft head by means of a locking element. The helping means includes a first member preferably in the form of a plunger for coming into direct pressing engagement with the attachment points provided at the inlay. The helping means also includes a second member, preferably a pulling member, which is movable relative to, preferably in opposition to the first member, and has a latching or clasping means which can be brought into pulling engagement with the receiving sleeve, preferably at its engagement element.

Another aspect of the invention relates to a helping means having a pulling member in the form of a sleeve surrounding the plunger, wherein at an axial end of the sleeve, radially inwardly protruding latching projections are formed and wherein the sleeve is operatively connected with the plunger via a coupling.

Another aspect of the invention relates to a helping means wherein the coupling is a lever mechanism preferably consisting of a hinged lever on one of the members among the plunger and the sleeve, wherein the lever is coupled via a joint to the respective other member.

Another aspect of the invention relates to a helping means wherein the coupling is a shaft-nut rotatably but also axially fixedly held relative to the sleeve and is in screwed engagement with the plunger. Alternatively, the coupling is a shaft-nut which is in screwed engagement with a thread on the plunger and is coupled to a rotationally fixed carrier which is axially moveable relative to the sleeve, wherein the carrier is fixed to the plunger.

Another aspect of the invention relates to a helping means wherein at least the plunger is provided with a preferably U-shaped longitudinal slot starting from the contact side with the inlay, wherein two flanks occur at which the plunger rests on the end face of the inlay.

Another aspect of the invention relates to a stabilization system that includes a polyaxial pedicle screw having a screwed shaft with a shaft head surrounded by a receiving sleeve in which is mounted an inlay biasable against the shaft head by means of a locking element. The stabilization system also includes a manually operable helping means having a first member for the selective provisional application of pressure directly to the inlay, and a second member for the selective provisional tensile loading of the receiving sleeve, which is parallel to the locking element in each case.

Another aspect of the invention relates to a stabilization system having a longitudinal member which is insertable in a transverse slot of the receiving sleeve, wherein at least the first member and preferably also the second member of the helping means is designed such that it engages around the longitudinal member.

Another aspect of the invention relates to a polyaxial pedicle screw, wherein the attachment points or engagement elements are configured as attachment points having form-locking fit or engagement elements having form-locking fit, preferably in the form of axial holes.

BRIEF DESCRIPTION OF THE DRAWINGS

The invention is explained in more detail below on the basis of a preferred exemplary embodiment with reference to the accompanying drawings.

FIG. 9a-9b shows a perspective view of the helping means according to the invention without coupling.

DETAILED DESCRIPTION

Figure 1:
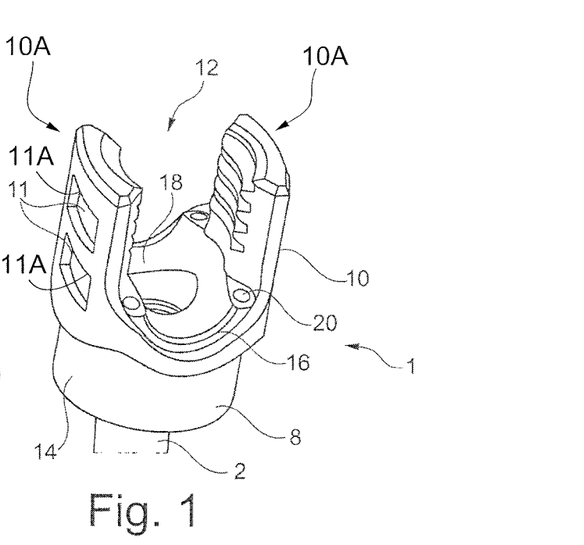
FIG. 1 shows the perspective view of a polyaxial pedicle screw according to a preferred exemplary embodiment of the invention.
Figure 2:
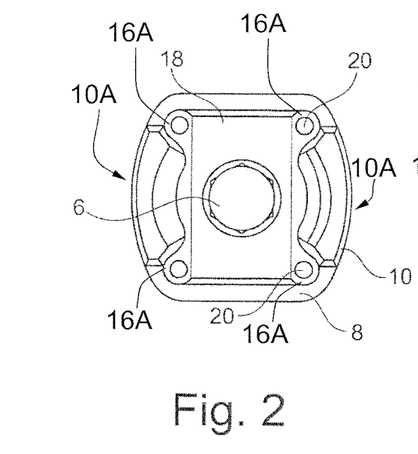
FIG. 2 shows the pedicle screw of FIG. 1 in top view.
Figure 3:
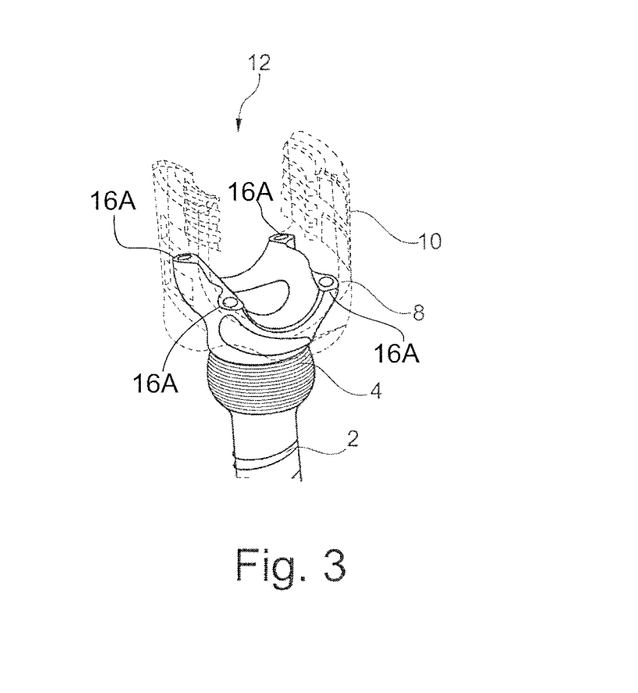
FIG. 3 shows a partially broken-line view of the pedicle screw of FIG. 1.

The polyaxial pedicle screw 1 shown in FIGS. 1 to 3 according to the preferred exemplary embodiment of the invention has a shaft or anchor 2 provided with an external thread, wherein at the proximal end of the shaft or anchor 2 a preferably spherical or at least semi-spherical shaft head 4 is formed or moulded. A tool engagement 6, for example for an "Imbus" key or a cross-headed screwdriver etc., is incorporated in the shaft head 4, in order to be able to screw the shaft 2 into the pedicle channel of a vertebra (not shown).

As can be seen from FIG. 3, the shaft head 4 forms at its transition region to the screwed shaft/shaft section 2 an undercut acting in the axial direction. This occurs in the present case by the shaft head diameter being chosen to be larger than the shaft diameter. Alternatively, it would also be conceivable to set the shaft head 4 apart from the remaining screwed shaft section 2 by means of a turned groove (not shown) at the proximal end section of the shaft 2.

According to FIG. 3 the shaft head 4 is grasped by a receiving sleeve 8 which (at first) is rotatably and pivotably held by the shaft head 4.

Specifically the receiving sleeve 8 has a cylindrical sleeve body 10 open on both sides, whose sleeve wall is slotted in a U-shape on the proximal end face, whereby there occurs a passing transverse groove (slot) 12 running essentially vertically to the sleeve axis. The receiving sleeve 8 is configured with an internal thread in the axial region towards the open side of the U-shaped slot 12, which according to FIG. 2 extends approximately until an axial mid-section of the sleeve 8. In the opposite lying axial region (e.g. at the axial distal end) of the sleeve 8, i.e. behind the slot base of the U-shaped slot 12, the receiving sleeve 8 is configured with a reduced diameter section 14 which narrows the sleeve's inner diameter at the front end and therefore represents an undercut. The diameter of the reduced diameter section 14 is thereby sized such that it is marginally bigger than the diameter of the screwed shaft section 2 but smaller than the diameter of the shaft head 4. Furthermore the inner diameter of the sleeve 8 or of the sleeve body 10 is marginally larger than the diameter of the shaft head 4. By means of the U-shaped longitudinal slots 12 there occur two flanks 10A lying radially opposite each other in the sleeve body 10, wherein engagement elements 11 are moulded or formed at each of the sleeve body's respective outer shell side. Here it presently concerns, for each flank, two axially spaced notches/pockets which form engagement undercuts 11A acting in the axial direction. Alternative to this, but equally possible, is to form strip-shaped protrusions on the external sleeve side of the flanks, which form the engagement elements 11. Basically therefore any form of engagement element is conceivable as long as an axial (provisional) tensile force can be applied in this way in the direction away from the shaft head 4 to the receiving sleeve 8.

A stamp-shaped power transfer member (inlay) 16 is put in place/inserted in the receiving sleeve 8. This inlay 16 is essentially formed by means of an inlay sleeve which lies on top of the shaft head 4 at one of its end faces. The other end face of the inlay sleeve (or simply inlay) 16 is widened into a flange-shaped collar 18 which in top view according to FIG. 2 is oval or rectangularly shaped, and in side view (see also FIG. 1) is formed into a concave channel/basin. (Blind) holes 20 are axially incorporated into radially projecting lugs 16A at the corners of the rectangle, wherein the holes 20 represent force introduction or attachment points for a tool-like external/separate helping means.

The receiving sleeve 8 and the inlay 16 are constructively adapted for each other such that the inlay 16 is displaceable at least over a predetermined distance in the receiving sleeve 6. Furthermore the inlay/pin 16 is inserted into the receiving sleeve 8 such that the basin which is formed/bulged at the inlay 16 on its end face diametrally connects both of the parallel U-shaped slots 12 with each other at the collar 18 and thus forms the support for an inserted longitudinal member, as is described in the following.

Figure 8:
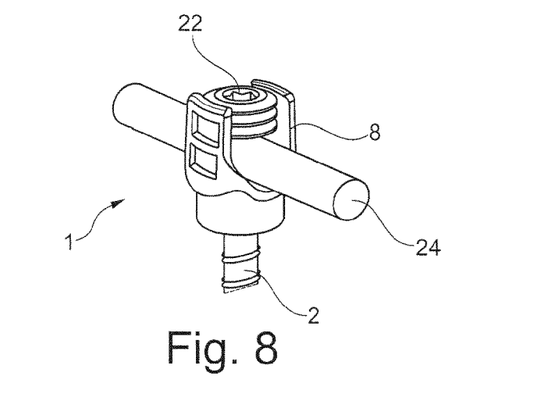
FIG. 8 shows the stabilization system in the readily assembled state and with helping means removed.

The operation of the polyaxial pedicle screw according to the preferred exemplary embodiment of the invention is described below in particular with reference to FIG. 8.

Consequently the pedicle screw 1 according to the invention is fixedly anchored at its screwed shaft 2 into the pedicle channel of a vertebra. A locking element preferably in the form of a grub screw 22 is screwed into the internal thread of the receiving sleeve 8, whereby the U-shaped slot(s) 12 is/are closed off at the receiving sleeve's 8 end face facing away from the shaft. In the lateral passage opening which is formed in this way, a longitudinal member 24 is inserted which longitudinally connects pedicle screws of different (axially adjacent) vertebra. The grub screw 22 is tightened so that the polyaxiality of the pedicle screw 1, i.e. the relative position between shaft 2 and receiving sleeve 8, is fixedly locked as desired and at the same time the longitudinal member 24 is fixedly clamped between the inlay 16 and the grub screw 22. In this locked state the screw force of the grub screw 22 is therefore transmitted via the longitudinal member 24 and the inlay 16 to the shaft head 4 and clamps it (by frictional fit) between the inlay 16 and the reduced diameter section 14 of the receiving sleeve 8.

The internal thread in the sleeve body 10 is sized such that it causes a self-locking. This means that the grub screw 22 can be released again only with considerable force. In addition, the receiving sleeve 8 is movable before the tightening of the grub screw 22 with respect to the shaft 2 such that no adjusting forces can be manually applied to the shaft 2 via the receiving sleeve 8, for example in order to change the position of the relevant vertebra.

To solve this problem an additional helping means 30 according to FIGS. 4 to 7 is provided.

This helping means 30 basically consists of a first member (plunger) 32, which can be brought into (form-locking) engagement with the inlay 16, and a second member (tension sleeve) 34 which can be brought into (form-locking) engagement with the receiving sleeve 8.

Figure 4:
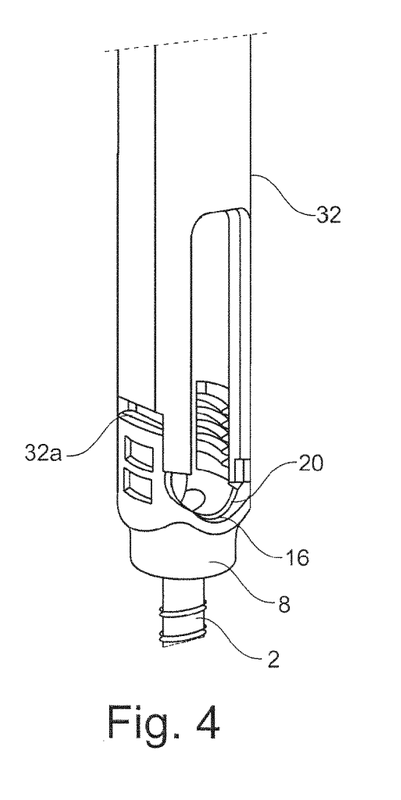
FIG. 4 shows the perspective view of a stabilization system according to a preferred exemplary embodiment of the invention consisting of the pedicle screw according to FIGS. 1 to 3 and a tool-like external helping means.

Specifically the first member 32 of the helping means 30 according to FIG. 4 is a plunger or piston, at one (distal) end face of which are formed a number of cones/spikes whose size and placement correspond to the (blind) holes 20 in the inlay 16. These are arranged due to the circular external outline of the collar 18 outside the footprint of the preferably circular locking element 22 such that the plunger 32 can still be brought into contact with the (blind) holes 20 for a provisional/temporary compressive force application of the inlay 16 when the locking element 22 is already screwed into the receiving sleeve 8 and is marginally supported via the inserted longitudinal member 24 against the inlay 16.

In the simplest case the plunger 32 is sleeve-shaped and completely surrounds the receiving sleeve 8. A slightly more complicated design according to FIG. 4 provides that the plunger 32 has two diametral axial grooves 32a at its distal end portion, which are sized so that both of the flanks of the receiving sleeve 8 can be axially introduced into it with substantially an exact fit. In this case therefore the mean diameter of the plunger 32 may approximately correspond to the mean diameter of the receiving sleeve 8. In addition the plunger 32 is additionally longitudinally slotted in a U-shape in accordance with the slots 12 in the receiving sleeve 8 such that these slots 12 are not closed off from the plunger 32 when in the set state, and thus a longitudinal member can be introduced also when the helping means is attached in the longitudinal slot.

Figure 5:
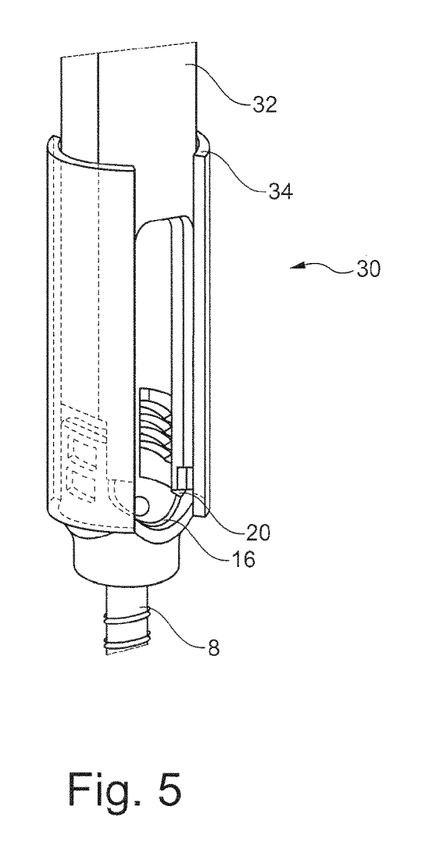
FIG. 5 shows a further perspective view of the stabilization system according to the invention with helping means in working position.
Figure 6:
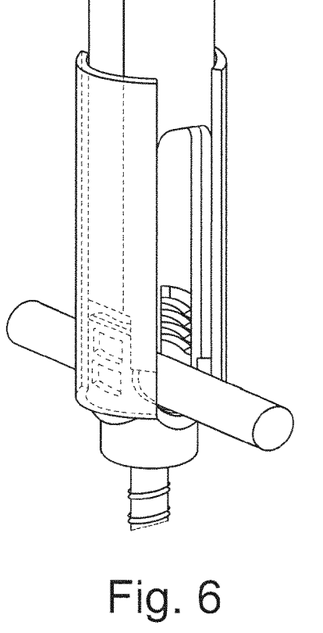
FIG. 6 shows a perspective view of the stabilization system according to the invention with helping means in working position and inserted longitudinal member.
Figure 7:
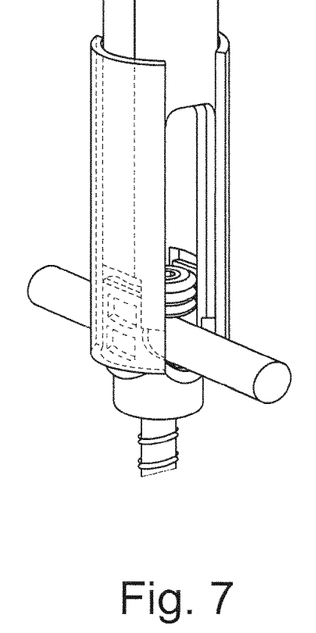
FIG. 7 shows a perspective view of the stabilization system according to the invention according to FIG. 6, additionally with locking element in place.
Figure 9A:
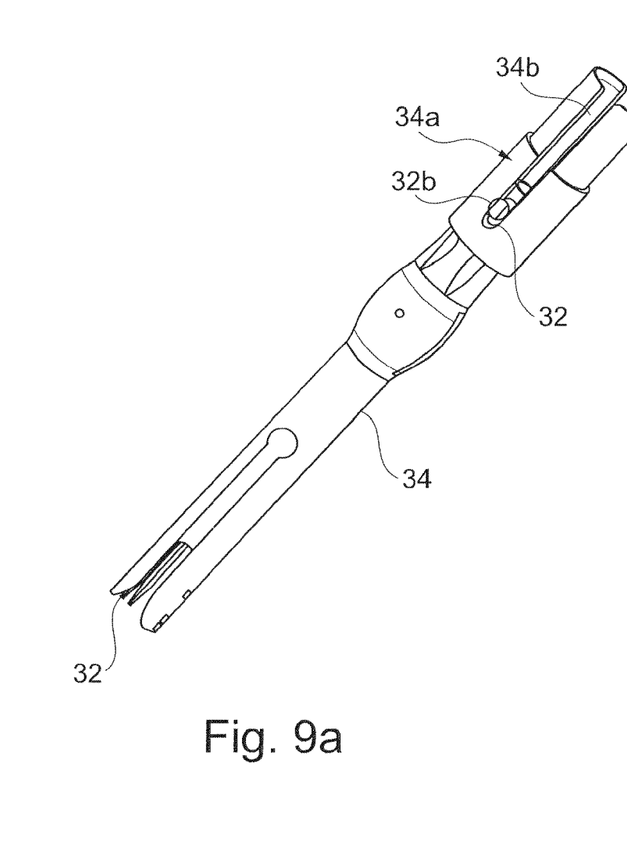
Figure 9B:
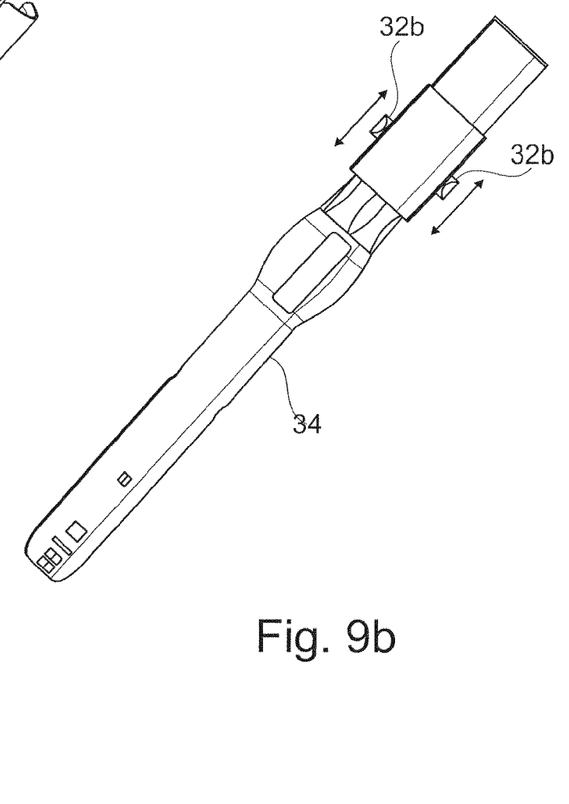

According to FIG. 5 the tension sleeve 34 is arranged movably around and relative to the plunger 32, wherein optionally another central/intermediate sleeve (not further depicted) between plunger 32 and tension sleeve 34 can be arranged. The tension sleeve 34 has at its distal end section a number of latching elements (not further shown) which with the notches/indentations 11 can be brought into releasable latching engagement with the flanks of the sleeve body 10. Finally the tension sleeve 34 is coupled at its opposite lying (proximal) end section with the plunger 32, such that both members are movable and thereby biasable via a coupling, as shown as an example in FIGS. 9 and 10.

For example the coupling may be a shaft-nut which is rotatable but axially fixedly placed at the tension sleeve 34 and can be screwingly engaged with the plunger 32. If consequently the shaft-nut is manually rotated, plunger 32 and tension sleeve 34 rotate relatively to each other in opposite directions. In this way the plunger 32 can be moved, by means of suitable manual turning of the shaft-nut, in the direction towards the inlay 16 and at the same time the tension sleeve 34 can be moved in the direction away from the inlay 16. In this case the receiving sleeve 8 can be provisionally/temporarily tightened with respect to the inlay 16 via the described helping means 30, wherein the shaft head 4 arranged in between is likewise provisionally/temporarily clamped.

Alternatively, for this purpose, it is also possible to form the tension sleeve 34 according to FIG. 9 with an external thread 34a at its proximal end section facing away from the pedicle screw, wherein the tension sleeve 34 is provided at this proximal end section with at least one longitudinal slot 34b (preferably two diametral longitudinal slots). In this case the plunger 32 has radially projecting drive pins 32b at its proximal end, which drive pins 32b protrude radially outwardly through the longitudinal slots 34b to the tension sleeve 34. According to FIG. 10 a shaft-nut 35 is screwed onto the external thread 34a of the tension sleeve 34, which shaft-nut 35 is in engagement with the drive pins 32b of the plunger 32. If now the shaft-nut 35 is rotated on the tension sleeve 34, a relative movement between the plunger 32 and the tension sleeve 34 is thus created.

Finally it should be pointed out at this point that other coupling forms are also conceivable which create a relative movement between plunger 32 and tension sleeve 34 by use of a lever effect or a gear reduction means.

The operation of the helping means 30 according to the invention is described more closely in the following, with reference to FIGS. 4 to 7.

Consequently, according to FIG. 4, the plunger 32 is first guided into the (blind) holes 20 of the inlay/pin 16, wherein the flanks are longitudinally guided on the sleeve body 10 in the axial grooves 32a of the plunger 32. In this relative position the slots 12 at the receiving sleeve 8 overlap with the U-shaped slot in the plunger 32, whereby a sort of lateral window is formed.

Subsequently the tension sleeve 34 is guided over the plunger 32 and latched with its latching protrusions in the notches 11 at the receiving sleeve 8. The tension sleeve 34, as clearly recognizable in FIG. 5, is also provided with U-shaped slots in accordance with the slot in the plunger 32, such that the lateral window furthermore remains open when the tension sleeve 34 is pulled over.

Figure 10:
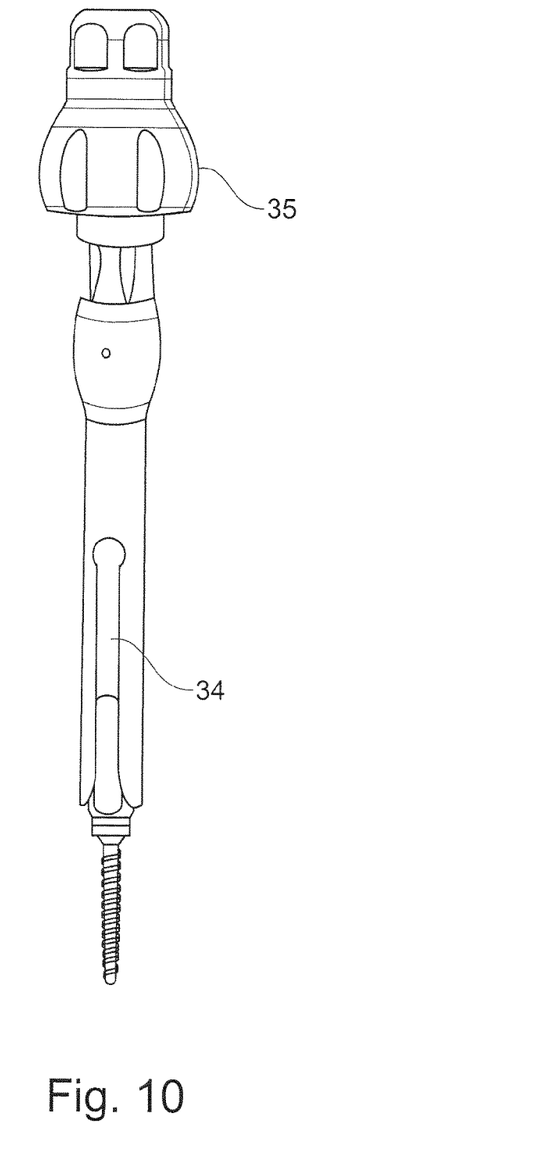
FIG. 10 shows a side view of the helping means according to FIG. 9, having a coupling in the form of a shaft-nut.

As soon as the helping means 30 is mounted on the inlay 16 and is latched with the receiving sleeve 8, the coupling (shaft-nut) 35, shown for example in FIGS. 9 and 10, and with it the shaft head 4 is provisionally/temporarily tensioned. According to the type of coupling, provisional preload forces are hereby achievable, which are the same as the preload forces of the actual locking element of the pedicle screw.

In this state a force from the helping means 30 via the receiving sleeve 8 can now be transmitted to the shaft 2, for example to adjust the vertebra. Subsequently the longitudinal member 24 is inserted according to FIG. 6 into the lateral window and the locking element, preferably the grub screw 22 already inserted in advance, is tightened, without the helping means 30 having to be removed in advance. With the tightening of the grub screw 22, the polyaxiality is finally locked such that the helping means 30 can be subsequently removed. In this way the assembly procedure is completed.

Finally the present invention is again summarized as follows:

Disclosed is a polyaxial pedicle screw 1 having a screwed shaft section 2 for anchoring the pedicle screw 1 in a vertebra, on one axial end of which a shaft head 4 is configured which is coupled in a rotating and/or pivoting manner as well as in a tensile force transmitting manner to a receiving sleeve 8 for a longitudinal support 24. The receiving sleeve 8 has a fastening means for selectively fixing the position of the receiving sleeve 8 with respect to the shaft section 2, said fastening means at least consisting of an inlay/bolt 16 mounted in the receiving sleeve 8 and acting on the shaft head 4 and a locking element 22 acting on the inlay 16. The inlay 16 is designed having attachment points or engagement elements 22, which are not covered or overlapped, for the provisional/temporary introduction of a pressure force on the inlay 16 parallel to the locking element 22.

Furthermore a tool-like helping means 30 is disclosed which can be attached (parallel to the locking element 22) with the inlay/pin 16 at its attachment points 20 for a provisional/temporary application of compressive force, and with the receiving sleeve 8 preferably at its engagement elements 11 for a provisional/temporary application of tensile force. Preferably the helping means 30 has two members, namely a pressing member 32 and a pulling member 34 which are coupled together such that a provisional application of pressure to the inlay 16 via one of the members necessarily leads to a tensile loading of the receiving sleeve 8 via the other member for achieving a balance of forces. Optionally the tool-like helping means 30 is provided at least partially as a disposable product. In particular the pressing member 32 should preferably be configured as a disposable member because it gets comparatively near to the vertebra of the patient and therefore can become contaminated with bodily fluids. In principle it is convenient if the entire helping means 30 is disposed of after its single use.

Finally a stabilization system according to the invention consists of the polyaxial pedicle screw 1, the helping means 30 and preferably a longitudinal member 24 which is inserted and fixedly clamped in the receiving sleeve 8.

The invention claimed is:

1. A polyaxial pedicle screw having a screwed shaft section for anchoring the pedicle screw in a vertebra,
wherein a shaft head is configured at an axial end of the screwed shaft section, said shaft head being pivotably and/or rotatingly coupled to a receiving sleeve for a longitudinal support,
wherein the receiving sleeve comprises a fastening means for selective positional fastening of the receiving sleeve with respect to the screwed shaft section, said fastening means at least comprising an inlay mounted in the receiving sleeve and acting on the shaft head, and a locking element acting via the longitudinal support on the inlay and screwed directly into the receiving sleeve,
wherein the inlay is configured with inlay engagement elements, which are not covered or overlapped by the locking element nor by the longitudinal support, for the introduction of a provisional compressive force parallel to the locking element on the inlay,
wherein the inlay engagement elements extend radially outwardly from an outermost circumference of the locking element in a direction perpendicular to the longitudinal axis of the locking element.

2. The polyaxial pedicle screw according to claim 1, wherein the receiving sleeve comprises a sleeve body open on both sides whose sleeve wall is slotted in a U-shape starting from a proximal end face, whereby there occur two flanks lying radially opposite each other, wherein the inlay engagement elements are located between the two flanks.

3. The polyaxial pedicle screw according to claim 2, wherein the inlay diametrically connects both of the U-shaped slots in the sleeve body.

4. The polyaxial pedicle screw according to claim 1, wherein the inlay has an outline deviating from a circle, at least at one axial portion.

5. The polyaxial pedicle screw according to claim 1, wherein the inlay is formed by an inlay sleeve, one end face of which is widened to a flange-like, oval or rectangular collar.

6. The polyaxial pedicle screw according to claim 5, wherein the inlay is formed as a rectangular collar, wherein radially projecting lugs are configured at the inlay at corners of the rectangular collar, and wherein the radially projecting lugs constitute the inlay engagement elements.

7. The polyaxial pedicle screw according to claim 1, wherein the receiving sleeve is configured or provided with at least one receiving sleeve engagement element via which an external provisional tensile force parallel to the locking element can be applied to the receiving sleeve.

8. The polyaxial pedicle screw according to claim 7, wherein the at least one receiving sleeve engagement element forms an engagement undercut on an external sleeve-side of the receiving sleeve.

9. The polyaxial pedicle screw according to claim 7, wherein the at least one receiving sleeve engagement element is provided with at least one indentation, pocket, undercut or strip-shaped projection.

10. The polyaxial pedicle screw according to claim 7, wherein the at least one receiving sleeve engagement element is provided with two axially spaced indentations, pockets, undercuts or strip-shaped projections.

11. The polyaxial pedicle screw according to claim 1, wherein the inlay engagement elements are configured as inlay engagement elements having form-locking fit in a plane perpendicular to an axial direction of the receiving sleeve.

12. The polyaxial pedicle screw according to claim 1, wherein a front face of the inlay is widened to a flange-like collar or formed as a concave trough.

13. A polyaxial pedicle screw having a screwed shaft section for anchoring the pedicle screw in a vertebra,
wherein a shaft head is configured at an axial end of the screwed shaft section, said shaft head being pivotably and/or rotatingly coupled to a receiving sleeve for a longitudinal support,
wherein the receiving sleeve comprises a fastening means for selective positional fastening of the receiving sleeve with respect to the screwed shaft section, said fastening means at least comprising an inlay mounted in the receiving sleeve and acting on the shaft head, and a locking element acting via the longitudinal support on the inlay and screwed directly into the receiving sleeve,
wherein the inlay is configured with inlay engagement elements, which are not covered or overlapped by the locking element or by the longitudinal support, for introduction of a provisional compressive force parallel to the locking element on the inlay,
wherein the receiving sleeve is configured or provided with at least one receiving sleeve engagement element via which an external provisional tensile force parallel to the locking element can be applied to the receiving sleeve,
wherein the inlay comprises a rectangular collar, wherein radially projecting lugs are configured at the inlay at corners of the rectangular collar, and wherein the radially projecting lugs constitute the inlay engagement elements.

14. The polyaxial pedicle screw according to claim 13, wherein the at least one receiving sleeve engagement element forms an undercut on an external sleeve-side of the receiving sleeve.

15. The polyaxial pedicle screw according to claim 13, wherein the at least one receiving sleeve engagement element is provided with at least one indentation, pocket, undercut or strip-shaped projection.

16. The polyaxial pedicle screw according to claim 15, wherein the at least one receiving sleeve engagement element is provided with two axially spaced indentations, pockets, undercuts or strip-shaped projections.

17. A polyaxial pedicle screw having a screwed shaft section for anchoring the pedicle screw in a vertebra,
wherein a shaft head is configured at an axial end of the screwed shaft section, said shaft head being pivotably and/or rotatingly coupled to a receiving sleeve for a longitudinal support,
wherein the receiving sleeve comprises a fastening means for selective positional fastening of the receiving sleeve with respect to the screwed shaft section, said fastening means at least comprising an inlay mounted in the receiving sleeve and acting on the shaft head, and a locking element acting via the longitudinal support on the inlay and screwed directly into the receiving sleeve,
wherein the inlay is configured with inlay engagement elements, which are not covered or overlapped by the locking element or by the longitudinal support, for introduction of a provisional compressive force parallel to the locking element on the inlay,
wherein the inlay engagement elements are configured as inlay engagement elements providing form-locking fit in a plane perpendicular to an axial direction of the receiving sleeve, and
wherein the inlay engagement elements are each formed as a concentric trough, hollow or recess having an indentation in the axial direction of the receiving sleeve providing form locking fit in all directions in the plane perpendicular to the axial direction of the receiving sleeve.

18. The polyaxial pedicle screw according to claim 17, wherein each concentric trough, hollow or recess defines an opening facing a proximal end of the receiving sleeve.

19. The polyaxial pedicle screw according to claim 17, wherein the inlay is formed such that it projects or is exposed, at least in portions, radially outwardly beyond an outermost circumference of the locking element in a direction perpendicular to a longitudinal axis of the locking element, whereby the inlay engagement elements occur at these radial portions which are not covered or overlapped by the locking element.

20. The polyaxial pedicle screw according to claim 17, wherein a front face of the inlay is widened to a flange-like collar or formed as a concave trough.

* * * * *